US010064618B2

(12) United States Patent
Allen

(10) Patent No.: US 10,064,618 B2
(45) Date of Patent: Sep. 4, 2018

(54) COMPRESSION BONE STAPLE

(71) Applicant: Zimmer, Inc., Warsaw, IN (US)

(72) Inventor: Drew Allen, Laguna Hills, CA (US)

(73) Assignee: Zimmer, Inc., Warsaw, IN (US)

(*) Notice: Subject to any disclaimer, the term of this patent is extended or adjusted under 35 U.S.C. 154(b) by 311 days.

(21) Appl. No.: 13/745,651

(22) Filed: Jan. 18, 2013

(65) Prior Publication Data

US 2014/0018809 A1 Jan. 16, 2014

Related U.S. Application Data

(60) Provisional application No. 61/589,252, filed on Jan. 20, 2012.

(51) Int. Cl.
*A61B 17/064* (2006.01)
*A61B 17/80* (2006.01)
*A61B 17/00* (2006.01)

(52) U.S. Cl.
CPC ........ *A61B 17/0642* (2013.01); *A61B 17/064* (2013.01); *A61B 17/0644* (2013.01); *A61B 17/8004* (2013.01); *A61B 17/809* (2013.01); *A61B 2017/00004* (2013.01); *A61B 2017/0088* (2013.01); *A61B 2017/00867* (2013.01); *A61B 2017/0645* (2013.01)

(58) Field of Classification Search
CPC .............. A61B 17/064; A61B 17/0642; A61B 17/0644; A61B 17/068; A61B 17/7044; A61B 17/8004; A61B 17/8023; A61B 17/8085; A61B 17/809; A61B 2017/00668; A61B 2017/0645; A61B 2017/0646

USPC .......................................... 606/297, 75, 219
See application file for complete search history.

(56) References Cited

U.S. PATENT DOCUMENTS 3,363,628 A * 1/1968 Wood .................. A61B 17/122
206/339
3,939,294 A   2/1976 Fieldhouse
3,939,828 A * 2/1976 Mohr et al. ................... 606/916
4,407,286 A * 10/1983 Noiles et al. ............... 227/175.1
4,838,254 A   6/1989 Gauthier
4,841,960 A   6/1989 Garner
4,852,558 A   8/1989 Outerbridge
5,053,038 A   10/1991 Sheehan
5,660,188 A   8/1997 Groiso (Continued)

OTHER PUBLICATIONS

International Search Report and Written Opinion, issued in respect to related application PCT/US2013/056289, filed Aug. 22, 2013.

*Primary Examiner* — Matthew Lawson
*Assistant Examiner* — Amy Sipp
(74) *Attorney, Agent, or Firm* — Schwegman Lundberg & Woessner, P.A.

(57) ABSTRACT

The present invention relates to devices and techniques for securing bone segments across a fracture site, and more particularly relates to bone staples for achieving compression between segments. A method and apparatus for interosseous bone fixation uses a compression staple, generally U-shaped, having a pair of legs with proximal ends interconnected by a bridge portion that is resilient and bowed, the staple having an initial configuration and capable of a tensioned configuration by spreading apart the legs by a certain amount causing the curvature of the bowed bridge to lessen and the legs to move towards each other with certain compressive spring force.

21 Claims, 11 Drawing Sheets

(56) References Cited

U.S. PATENT DOCUMENTS

| | | | |
|---|---|---|---|
| 5,662,655 A | | 9/1997 | Laboureau et al. |
| 5,941,890 A | * | 8/1999 | Voegele et al. ............... 606/151 |
| 6,059,787 A | | 5/2000 | Allen |
| 6,190,401 B1 | * | 2/2001 | Green .................... A61B 17/06 |
| | | | 227/902 |
| 6,336,928 B1 | * | 1/2002 | Guerin et al. ............... 606/282 |
| 6,348,054 B1 | | 2/2002 | Allen |
| 6,783,531 B2 | | 8/2004 | Allen |
| 8,021,403 B2 | * | 9/2011 | Wall et al. .................... 606/297 |
| 8,137,351 B2 | * | 3/2012 | Prandi ............................ 606/75 |
| 2003/0167072 A1 | | 9/2003 | Oberlander |
| 2005/0096660 A1 | | 5/2005 | Allen |
| 2005/0277933 A1 | * | 12/2005 | Wall et al. ...................... 606/61 |
| 2006/0247681 A1 | * | 11/2006 | De Canniere et al. ....... 606/219 |
| 2007/0093839 A1 | * | 4/2007 | Beckendorf ....... A61B 17/0642 |
| | | | 606/75 |
| 2008/0147125 A1 | * | 6/2008 | Colleran et al. ............. 606/280 |
| 2008/0217376 A1 | * | 9/2008 | Clauson et al. ............ 227/181.1 |
| 2008/0319443 A1 | * | 12/2008 | Focht et al. ..................... 606/75 |
| 2010/0063506 A1 | * | 3/2010 | Fox et al. ........................ 606/75 |
| 2010/0125275 A1 | * | 5/2010 | Kinmon et al. ................ 606/75 |
| 2010/0237128 A1 | * | 9/2010 | Miller et al. ............... 227/175.1 |
| 2010/0256765 A1 | * | 10/2010 | Butler et al. ............... 623/17.16 |
| 2010/0292715 A1 | * | 11/2010 | Nering et al. ................ 606/151 |
| 2012/0024937 A1 | | 2/2012 | Allen |
| 2012/0228355 A1 | * | 9/2012 | Combrowski et al. .... 227/175.1 |
| 2013/0030437 A1 | * | 1/2013 | Fox ................................. 606/75 |

\* cited by examiner

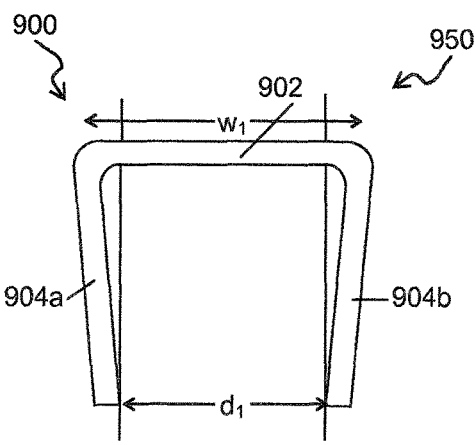
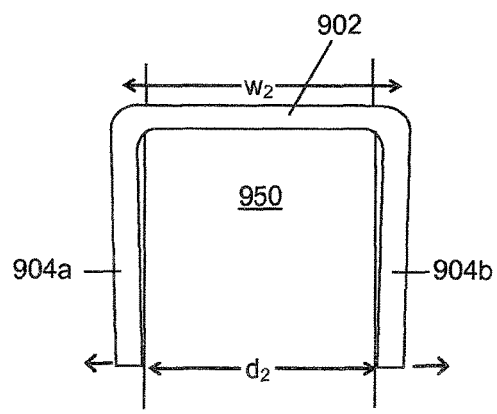
FIG. 9A                              FIG. 9B
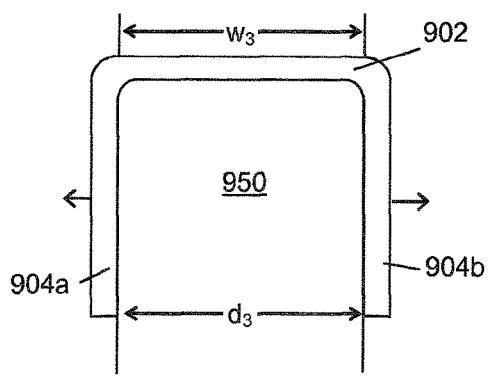
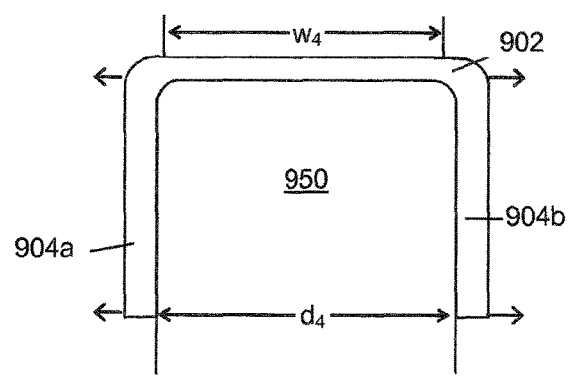
FIG. 9C                              FIG. 9D

COMPRESSION BONE STAPLE

This application claims priority under 35 U.S.C. 119(e) to commonly assigned U.S. Provisional Application Ser. No. 61/589,252, entitled Compression Bone Staple, and filed on Jan. 20, 2012, which application is herein expressly incorporated by reference, in its entirety.

TECHNICAL FIELD

The present invention relates to devices and techniques for securing bone segments across a fracture site, and more particularly relates to bone staples for achieving compression between segments.

BACKGROUND

In treating a bone fracture it is common practice to fasten one bone segment to the other so as to stabilize and immobilize them for the duration of the bone consolidation process. Thus there is the technique of internal fixation or direct mechanical fastening of the bone segments.

Traditionally, fixation has been accomplished by variety of apparatus and techniques, the more common involving the use of metallic fastening devices such as screws, connector plates (secured to the bone by screws), pins and clips. These methods invariably involve the drilling of screw holes in the bone and the use of related equipment such as drill hole templates.

Conventional U-shaped clips have also been used, the clip legs being installed one each in holes in the opposing bone segments. The rigid structure of such clips, like the other fixation devices mentioned above, provides rigid immobilization of the fracture zone. Such devices also serve to maintain the distance between segments. However, among other things, such distance hinders compression induced by contractions of skeletal muscles in some cases, and prevents the establishment of compressive force between the bone segments which is favorable to bone consolidation or knitting. In this regard the concept of creating dynamic compressive force across an osteotomy or bone fracture site has become recognized as a technique to promote primary bone healing, i.e. consolidation that is faster and of better quality.

Thus there has evolved a number of fastening devices such as clips and the like, designed to deliver compression. Accordingly in U.S. Pat. No. 3,939,294 there is provided a clasp or clip of spring material having a pair of spaced-apart, inwardly inclined legs connected by a Z-shaped upper portion. Sloped holes are drilled in adjoining bone segments and tools are used to manipulate and install one leg, and then the other leg is pulled toward the other hole, spreading the Z-shaped elastic portion, and then inserted in the other hole. Unfortunately this method requires the drilling of specially sloped holes, involves multiple steps and is time-consuming, and like the conventional rigid fastening techniques, requires relatively large surgical opening. Also, the manual installation of the clip using hemostats and the like is difficult, requires meticulous skill and handling.

In U.S. Pat. No. 4,838,254, the legs of a pair of metallic clips are inserted in pairs of specially angled bores in respective opposing bone segments. The exposed tops of the two installed clips then serve as fastening heads for a spring that is connected between the clips.

In U.S. Pat. No. 4,841,960 the disclosed compression clip is essentially a clip with opposing legs that are installed in pre-drilled holes and features a crimpable web that joins the top ends of the legs. A crimping tool is used to crimp the web in an effort to set up compression between the embedded legs.

U.S. Pat. No. 4,852,558 also requires manual installation of separate legs in pre-drilled holes, the tops of the install legs then being interconnected with a ratchet mechanism which must be operated to draw the legs together. This design appears inherently limited regarding adjustability and maintenance of constant pressure. In U.S. Pat. No. 5,660,188 the two legs of a clip must also be installed in pre-drilled holes. The clip has a bridge of two side-by-side crimpable elements, and the jaws of a crimping tool must be used on the embedded clip to deformingly spread apart these elements, causing the legs to draw to each other. The foregoing techniques involving crimpable clips all appear to be imprecise in setting up suitable compressive forces, require hole drilling and related problems, and do not lend themselves to minimizing the size of the surgical opening.

In view of the limitations of the afore-mentioned methods, stapling has been looked to as a way to produce compression. Thus in U.S. Pat. Nos. 5,053,038 and 5,662,655, staples are applied to the bone by a powered stapler. However, there is little apparent precision in establishing the desired compressive forces.

Thus, there remains a need for bone staples for achieving compression between segments.

SUMMARY

In view of the foregoing it is a general object of the present invention to provide an improved method and staples for securing bone segments.

A more particular object is to provide quick and simple, yet effective method for fastening bone segments with compressive force between opposing bone ends.

Another object to provide such a method that minimizes or reduces the size of the required surgical opening and associated trauma.

A further object to provide a method of bone stapling that minimizes or reduces trauma to the bone tissue during implantation of the staple legs.

Yet another object is to provide a method for stapling that maximizes or increases the capability of establishing a dynamic compression level that is optimal for enhanced osseous healing.

A still further object is to provide simple, effective bone fixation technique that is relatively easy to learn and practice.

Still another object is to provide bone compression staples in which there is a range of compressive forces that can be applied based on the selection of compression staple.

These and other objects of the present invention are achievable by way of the present invention of a bone stapling method that uses a generally U-shaped staple having pair of spaced apart legs with proximal ends interconnected by bridge that has at least one resilient curved portion, whereby spreading apart of the legs lessens the curvature of the curved portions which brings the staple to a tensioned configuration in which one leg is resiliently urged towards the other. In a preferred embodiment it is seen that the bridge portion comprises a single bowed spring element, the curvature of which is "gull-wing" shaped and lies in a plane normal to the axes of the staple legs.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein expressly incorporated by reference, in their entirety, to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 provides an example of a method of preparing a compression staple for delivery to a target in accordance with an embodiment of the invention.

FIG. 9 provides another example of a method of preparing a compression staple for delivery to a target. FIG. 9A shows contact between an expanding loading mechanism and the ends of the legs of the compression staple. FIG. 9B shows further expansion of the expanding loading mechanism, thereby causing the legs of the compression staple to torque slightly outward. FIG. 9C shows contact between the expanding loading mechanism and the ends of the bridge of the compression staple. FIG. 9D shows an expanding loading mechanism that has caused the compression staple to expand at the bridge in preparation for delivery.

FIG. 10 illustrates an additional exemplary method of preparing a compression staple for delivery to a target.

FIG. 11 provides an example of states of a compression staple as it is delivered to a target.

DETAILED DESCRIPTION

While preferred embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention provides systems and methods for connecting bone fragments. Various aspects of the invention described herein may be applied to any of the particular applications set forth below or for any other types of bone staples or connection mechanisms. The invention may be applied as a standalone system or method, or as part of an integrated medical treatment or orthopedic system. It shall be understood that different aspects of the invention can be appreciated individually, collectively, or in combination with each other.

The present invention relates to devices and techniques for securing bone segments across a fracture site, and more particularly relates to compression staples for achieving compression between segments.

Figure 1:
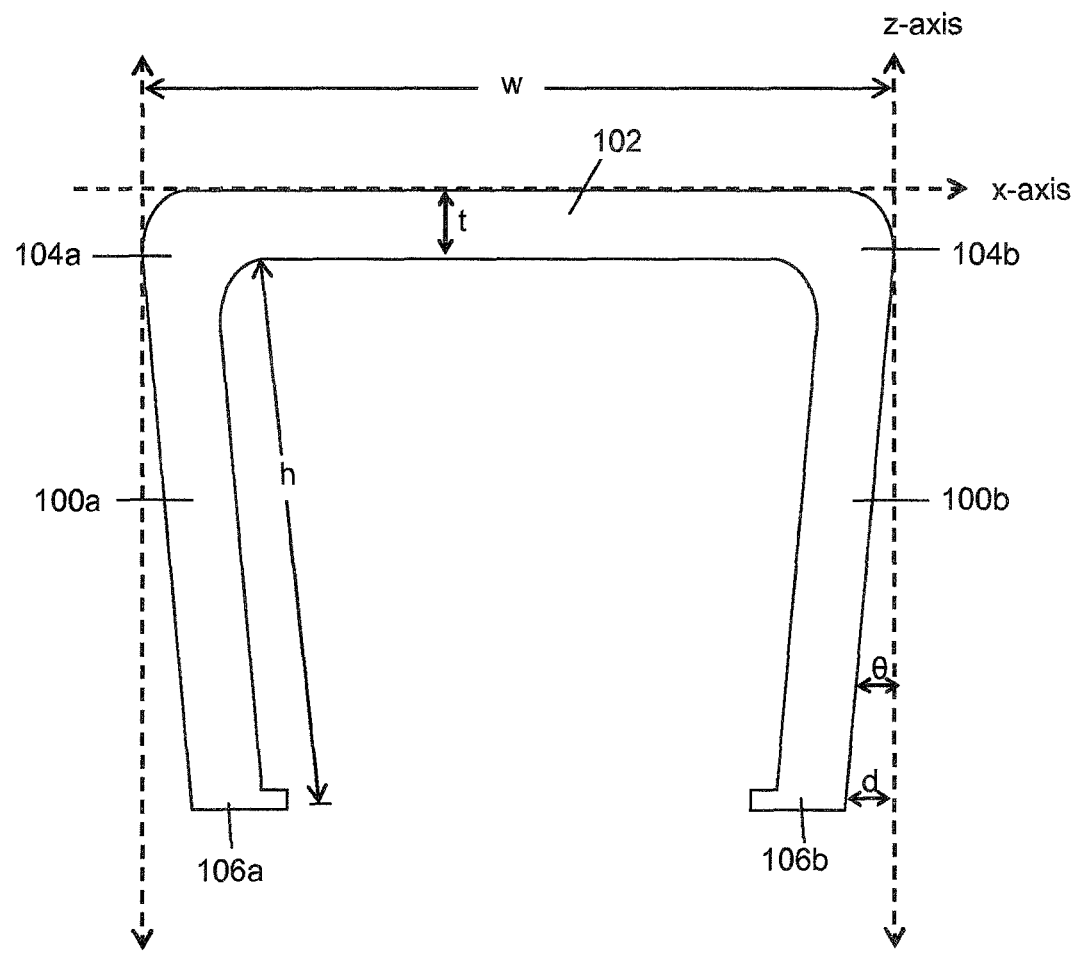
FIG. 1 shows a schematic of a compression staple provided in accordance with an embodiment of the invention.

FIG. 1 shows a schematic of a compression staple provided in accordance with an embodiment of the invention. A compression staple may have a plurality of legs 100a, 100b that may be connected to one another via a bridge 102. The compression staple may have two or more legs, wherein a leg may have a proximal end 104a, 104b, and a distal end 106a, 106b. The proximal end of the leg may be connected to the bridge. The legs may connect to a bridge at the ends of the bridge. The connection between the legs and bridge may be rounded or may be angled. The distal end of the leg may be away from the bridge. In some embodiments, a leg may terminate in a foot, at the distal end of the leg 106a, 106b.

Any dimensions may be provided for a compression staple. For example, a leg of the compression staple may have a height h. The height of the compression staple may be greater than, less than, or equal to about 1 mm, 2 mm, 3 mm, 5 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 27 mm, 30 mm, or 35 mm. A bridge of the compression staple may have any width w. The width of the compression staple may be the dimension of the compression staple extending along the x-axis. The width of the compression staple may be less than or equal to the length along the bridge of the compression staple. The width of the compression staple may be greater than, less than, or equal to about 1 mm, 2 mm, 3 mm, 5 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 27 mm, 30 mm, 35 mm, 40 mm, 45 mm, or 50 mm. The height of the compression staple may be greater than, less than, or equal to about the width. In some embodiments, the ratio of the height to width (h:w)

may be greater than, less than, or equal to about 5:1, 4:1, 3:1, 2:1, 1.5:1, 1.3:1, 1.2:1, 1.1:1, 1:1, 1:1.1, 1:1.2, 1:1.3, 1:1.5, 1:2, 1:3, 1:4, or 1:5. The bridge may have any thickness t. For example, the thickness of the compression staple may be greater than, less than, or equal to about 0.1 mm, 0.5 mm, 1 mm, 1.5 mm, 2 mm, 2.5 mm, 3 mm, 3.5 mm, 4 mm, or 5 mm. The legs may also have any thickness value. The leg thickness may be greater than, less than, or equal to about the bridge thickness.

The legs of the compression staple may have the same length h. Alternatively, they may have differing lengths. Legs may have elongated members between proximal and distal ends. The legs may be straight, curved, bent, or have any other configuration. The profile of the legs may remain the same during use, or may change.

A compression staple may be a bone staple capable of securing bone segments. A bone stapling method for compressively securing adjoining bone segments may use a resilient compression staple that may have legs with an initial convergent configuration with respect to each other. The legs may be resiliently extendible into parallel relationship, in which configuration a predetermined amount of spring force may urge the legs towards their initial convergent orientation. For example, in their natural state, the legs may have a convergent configuration where they are angled toward one another at an angle θ from having a parallel configuration (e.g., angle θ from a z-axis, wherein the z-axis is orthogonal to the x-axis). The distal end of a leg of the compression staple in its relaxed state may be a distance d from the position it would hold if the legs were parallel to one another.

The bone stapling method may include holding the normally convergent staple in its legs-parallel configuration (e.g., angle θ=0), positioning the so-tensioned staple with its ends aligned respectively with adjacent bone surfaces; and then driving and embedding the legs of the tensioned staple in the bone segments and releasing the embedded staple, whereby the bone segments are joined, and opposing surfaces of the bone segments are caused to be pressed into engagement with each other with a certain amount of compressive force.

The bone stapling method may also include stretching a resilient bridge of the compression staple from its relaxed state. For example, the bridge of a bone staple may be stretched and the staple delivered to the bone segments. The legs of the tensioned staple may be delivered and released, whereby the bone segments are joined, and the bridge and/or legs provide a certain amount of compressive force.

The compressive forces may range between about 25-45 lbs. of compression, preferably between about 30-40 lbs. of compression. In some embodiments, the compressive forces provided by the staple may be greater than, less than, or equal to about 5 lbs, 10 lbs, 15 lbs, 20 lbs, 25 lbs, 30 lbs, 35 lbs, 40 lbs, 45 lbs, 50 lbs, 60 lbs, 70 lbs, 80 lbs, 90 lbs, or 100 lbs of compression. In some embodiments, the amount of compression provided by the legs of the staple may be relatively stable over the length of the legs. For example, in various embodiments, the amount of compression provided by the staple legs may vary by less than 80%, 70%, 60%, 50%, 40%, or 30% over the length of the staple legs. Any of the compression values described herein may be provided at the distal ends of the legs, the proximal ends of the legs, or anywhere in between. In some embodiments, the ratio of compressive forces provided by the staple to a dimension of the staple (e.g., length of leg, length of bridge), may be any of the compressive forces listed elsewhere herein to any of the dimension measurements mentioned elsewhere herein.

A compression staple may be a metallic staple. For example, the staple may be fabricated of a surgical grade, bio-compatible metal, such as stainless steel, titanium alloy or other suitable alloy In various embodiments, the staple may be fabricated from a ceramic material, bioabsorbable material, bioresorbable material, plastics, crystalline, polyether ether ketone (PEEK), nitinol, or other material that is compatible with providing the desired compression force. The staple may be fabricated from a material having a desired stiffness. For example, the staple may be fabricated from a material having a stiffness of less than, greater than or equal to about 100 GPa, 110 Gpa, 120 Gpa, 130 Gpa, 140 Gpa, 150 Gpa, 160 Gpa, 170 Gpa, 180 Gpa, 190 Gpa, 200 Gpa, 210 Gpa, 220 Gpa, 230 Gpa, 250 Gpa, 270 Gpa, 300 Gpa, or 350 Gpa. In some examples, the staple may be fabricated from a material having a yield strength or a tensile strength of less than, greater than or equal to about 250 Mpa, 300 Mpa, 350 Mpa, 400 Mpa, 450 Mpa, 500 Mpa, 550 Mpa, 600 Mpa, or 650 Mpa.

The staple may be formed from a single integral piece. The staple may be formed from a single continuous piece. In some embodiments, the staple may be formed from a single material, such as a single metal. In some instances, the staple is not made of multiple pieces. Alternatively, the staple may have one or more piece.

The bridge may hold the legs in approximate parallel relationship, and may additionally be selected to act as a spring by the flexing of its bow when the legs are spread apart. This may impart an inward reacting force between the legs proportional to the degree of their displacement. It will be appreciated that the dimensions, gauge and curvature of the bridge may be selected such that it can be flexed to a tensioned state that may deliver the compression requirements of the bone fixation to which staple is to be applied.

The compression staple may have any configuration or feature, including those described elsewhere herein.

Figure 2:
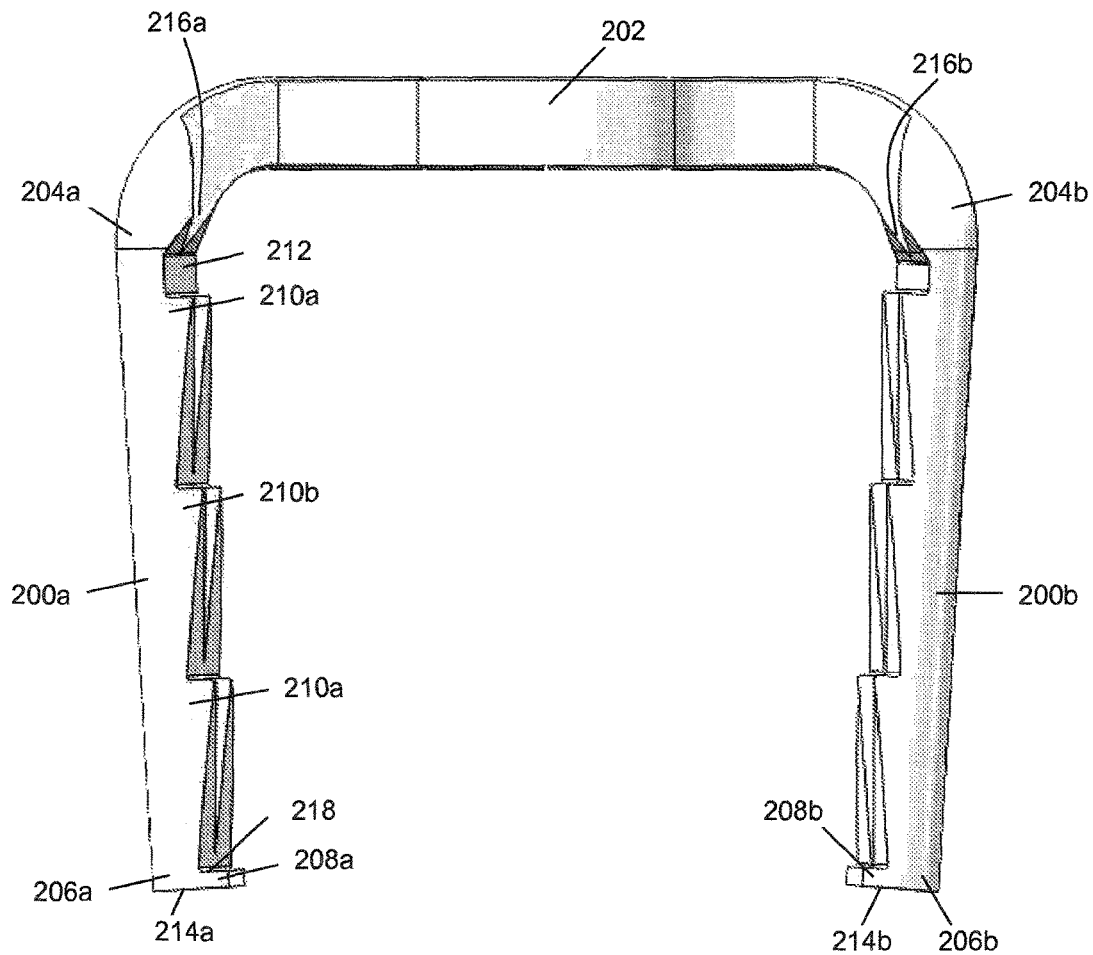
FIG. 2 is side view of a compression staple according to an embodiment of the invention.

FIG. 2 is a side view of a compression staple according to an embodiment of the invention. In a preferable embodiment of the invention, a compression staple may have a pair of legs 200a, 200b with flat front ends 206a, 206b and a bridge 202 that interconnects rear end portions 204a, 204b of the legs.

The staple legs and bridge may be formed from a rod or strip having suitable strength and spring properties. The material used to form the staple may include any materials described elsewhere herein.

The rear portions 204a, 204b of the legs may be curved to meet the bridge 202. Alternatively, they may provide a sharp angle. The bridge may have a flat side profile. Alternatively the bridge may be curved. The bridge may be shaped or curved to fit the contour of a bone surface.

In some embodiments, the legs may have an elongated shape between their front and rear ends. The legs may be substantially straight. Alternatively, the legs may be curved or bent.

The opposing inside surfaces of legs may be provided with surface features 210a, 210b, 210c, such as ramps, teeth, serrations or barbs. The surface features may include protruding portions. The surface features may have a ratchet configuration. For example, the surface features may include one or more asymmetrical teeth that may travel more easily in one direction than another. For example, the leg of a bone staple may more easily enter bone tissue than be removed from the bone tissue. The surface features may be angled so that there is a more gradual angle on the side of the surface feature closer to the front end portion of the leg, and a sharper angle on the side of the surface feature closer to the rear end portion of the leg. The surface features may be straight, curved, or any combination thereof.

The surface features may be provided along the length of the staple legs. The surface features may be provided along the entire length of the legs or along a portion of the length of the legs. The surfaces features may be provided along a distal portion of the legs. In some embodiments, a portion of the legs 212 do not include the surface features. Any number of surface features may be provided on a leg. For example, one or more, two or more, three or more, four or more, five or more, six or more, eight or more, or ten or more rows of teeth, ramps, serrations, or barbs may be provided.

A groove 216a, 216b may extend along a length of the leg. In some embodiments, each leg may have a groove therein. The grooves may be provided on the sides of the legs facing one another. The groove may be described in greater detail elsewhere herein.

As previously described, the surface features may be provided along the inside surface of the legs (the surfaces of the legs facing one another). In other embodiments, the surface features may be provided on the outer surface of the legs or the side surfaces of the legs, or any combination of surfaces of the legs. The surface features may be provided on a side of the leg which experiences a compressive force. The surface features may be provided on a side of the leg that is pressed against bone. In this regard it is noted that, inasmuch as the insides of legs will be pressed against bone mass when they are embedded in a manner to be described, the size of such surface features can be advantageously minimized or reduced, which minimizes or reduces trauma to the bone tissue during their implantation.

In some embodiments, front end portion of a leg may include a flat surface 214a, 214b with a foot 208a, 208b extending beyond the leg to form a ledge. In one embodiment, the presence of a flat surface at the base of the staple legs avoids irritation of the tissue into which the staple is inserted. The surface at the base of the staple legs may alternatively be rounded, pointed, tapered, bumped, notched, or have any other configuration.

The foot at the base of the leg may provide an increased pull-out force, i.e. the force required to remove the staple is increased compared to a staple without a foot or ledge at the base of the stable legs. In some embodiments, a staple may have a pair of legs, each terminating in a foot. The pair of feet may be configured with their ledges facing one another, in the direction of a compression force provided by the staple. The compression force may cause the feet with the ledges to be forced against the bone tissue, and the ledge may provide additional force that may make it more difficult to remove the staple. The length of the foot (e.g., length of the ledge provided in an x-axis direction illustrated in FIG. 1) may be greater than the thickness of a leg. The length of the foot may or may not be greater than the largest protruding sections of the surface features of a leg. The ledge of the foot may protrude greater than, less than, or equal to about 0.1 mm, 0.2 mm, 0.3 mm, 0.4 mm, 0.5 mm, 0.7 mm, 1.0 mm, 1.2 mm, 1.5 mm, or 2.0 mm. The top surface of the foot 218 may be flat. Alternatively, the top surface of the foot may be angled, curved, or hooked. The top surface of the foot may be within 3 mm, 2 mm, or 1 mm of the end of the front end portion of the leg.

Figure 3:
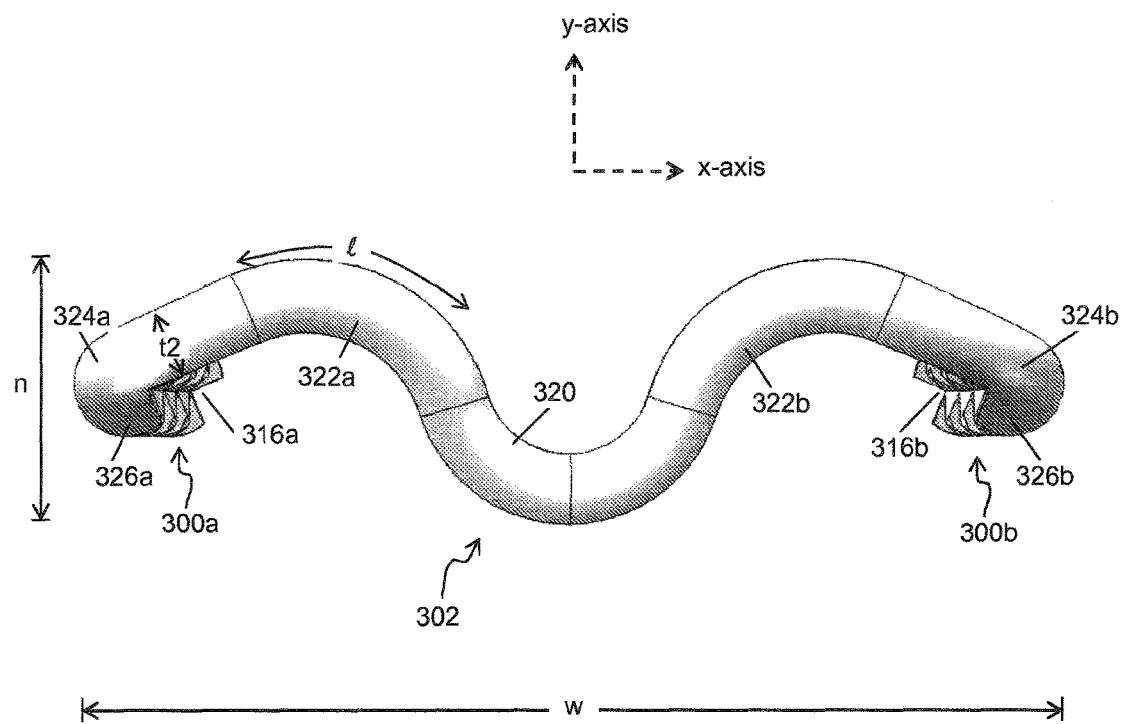
FIG. 3 is top plan view of a compression staple.

FIG. 3 is top plan view of a compression staple. A bridge 302 may connect two legs 300a, 300b of the staple.

The bridge 302 of the staple may be curved. The curvature of the bridge may be in a "gull-wing"-shape or S-shape. An example of a gull-wing shape is provided in FIG. 3. It is also contemplated under the invention that the curvature of the bridge can take other forms compatible with the "gull-wing"-shape or S-shape.

The bridge may be shaped to be symmetrical about a y-axis that may pass through the center of the bridge. Alternatively, the bridge need not be symmetrical about the y-axis. The bridge may have a width w extending in an x-direction parallel to the x-axis. The bridge may have a depth n extending in a y-direction parallel to the y-axis. In some embodiments, the ratio of the width to depth of the bridge (w:n) may be greater than, less than, or equal to about 10:1, 9:1, 8:1, 7:1, 6:1, 5:1, 4:1, 3:1, 2.5:1, 2:1, 1.5:1, or 1:1. The bridge may have a length l along the length of the bridge as it curves. The width w of the bridge may be less than the length l of the bridge. In some embodiments, the ratio of the width to length of the bridge (w:l) may be greater than, less than, or equal to about 1:5, 1:4, 1:3.5, 1:3 1:2.5, 1:2.2, 1:2, 1:1.7, 1:1.5, 1:1.3, or 1:1.1.

The bridge may include a plurality of curves. For example, the bridge may have a central curve 320, and one or more peripheral curves 322a, 322b. The central curve may be directed in a first direction, while the peripheral curves may be directed in another direction. The peripheral curves may be directed in a direction opposing the first direction. For example, the central curve may curve upward toward a positive y-direction, while the peripheral curves may curve downward toward a negative y-direction. In some embodiments, the bridge may include one or more curves, two or more curves, three or more curves, four or more curves, five or more curves, or any number of curves. The curves may be provided so that they curve in alternating fashion.

The curvature of the central curve 320 may be greater than, less than, or equal to the curvature of the peripheral curves 322a, 322b. In one example, the curvature of the central curve may be greater so that the peripheral curves do not bend as much as the central curve.

The ends 324a, 324b of the bridge may be located in the y-direction between the central curve and the peripheral curves. For example, the central curve may extend more in a negative y-direction than the bridge ends, and the peripheral curves may extend more in a positive y-direction than the bridge ends. In some embodiments, the end portions of the bridge may be relatively straight. A peripheral curve may lead into a straight end portion.

A gull-wing shaped bridge may advantageously provide a desired degree of compression force. The gull-wing shape may provide a greater degree of compression force per length l of bridge, width w, depth n, and/or thickness t of bridge than some other shapes (e.g., some shapes with two or fewer curves).

The legs 300a, 300b may extend from the bridge 302 at the ends of the bridge 324a, 324b. A groove 316a, 316b may extend along the length of the legs. In various embodiments, the staple legs may contain grooves on the internal face of the staple legs in order to allow smooth delivery of the staple from a staple-delivery means. For example, a staple gun or other staple delivery mechanisms may have a portion that may engage with the grooves of the legs. A staple delivery mechanism may have one or more guide that may fit into the groove. For example, the inside surfaces of the staple bridge and legs may be adapted to slidably engage a staple-feeding ramp structure, or other staple loading mechanism as described elsewhere herein. The staple delivery mechanisms and/or loading mechanisms may have guide or features that may fit into the grooves, and that may permit a desired tension force to be exerted on the staple legs via the groove.

The grooves may permit mechanisms to engage with the staple, and exert a force on the staple, thereby flexing the staple to a tensioned state. Utilizing grooves in the staple may permit the staple to engage with the staple delivery and/or loading mechanism in a controlled manner. This may be advantageous when providing a controlled amount of force to the staple, and flexing the staple to a desired state. The groove may keep the staple in place while it is tensioned and prior to delivery. Such configurations may provide a high degree of precision and/or control.

Figure 7:
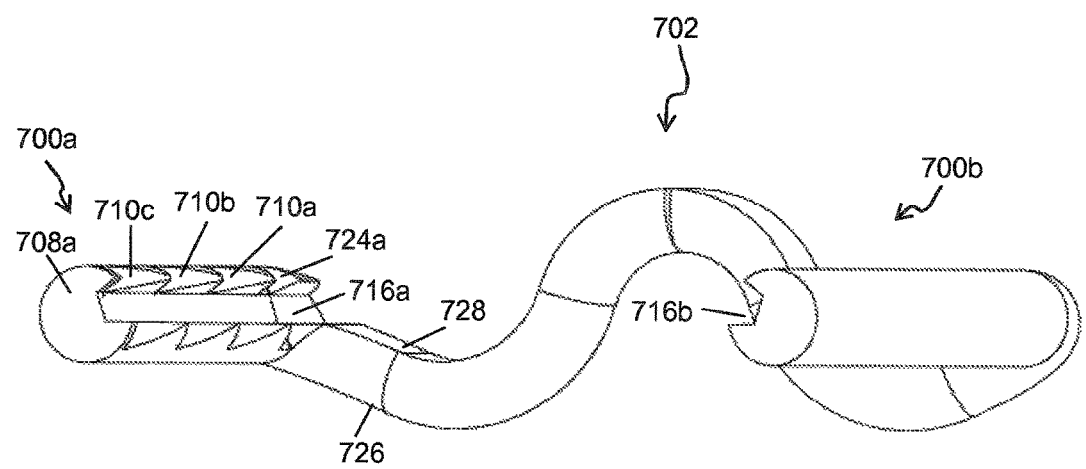
FIG. 7 is a lower perspective view of a compression staple provided in accordance with an embodiment of the invention.

Such grooves may be of any configuration. For example, such grooves may be wedge-shaped as shown in FIG. 3. The wedge may have any size or angle (e.g., about 150 degrees, 120 degrees, 90 degrees, 60 degrees, 30 degrees). Alternatively, such grooves may have a flat edge, as shown in FIG. 7. The grooves may have any number of sides in the staple legs (e.g., one side, two sides, three sides, four sides, five sides, or more). The grooves may include flat sides and/or curved sides. The grooves may be dimensioned or shaped to accept a guide feature for a staple delivery and/or loading mechanism.

It will be evident that there can be several variations of compression staples according to the principles of the invention. For example, staple legs can have various cross sectional configurations, including circular, elliptical, diamond-shaped, square, triangular, rectangular, pentagonal, hexagonal, heptagonal, octagonal, or any other shape. The staple leg cross-section may include and/or incorporate the groove shapes.

An end portion of a bridge 324a, 324b may include a hooked or protruding portion 326a, 326b. The hooked or protruding portion may be formed in part by the groove 316a, 316b. The hooked or protruding portion of the bridge end may extend beyond a lateral thickness t2 of the bridge. The lateral thickness t2 of the bridge may remain the same along the length of the bridge or may vary along the length of the bridge. The bridge end may be rounded or may include one or more edges.

In some embodiments, the hooked or protruding portions of the bridge ends may be formed by portions of the bridge that are carved out due to the groove. A side of the bridge may be flattened and/or carved out to match the contour of the groove. This may result in a lesser lateral thickness of the bridge than if no groove or carveout existed. In some embodiments, the central curved portion may be curved so that the lowest (protruding) portion of the curve is on the side of the carveout.

Figure 4:
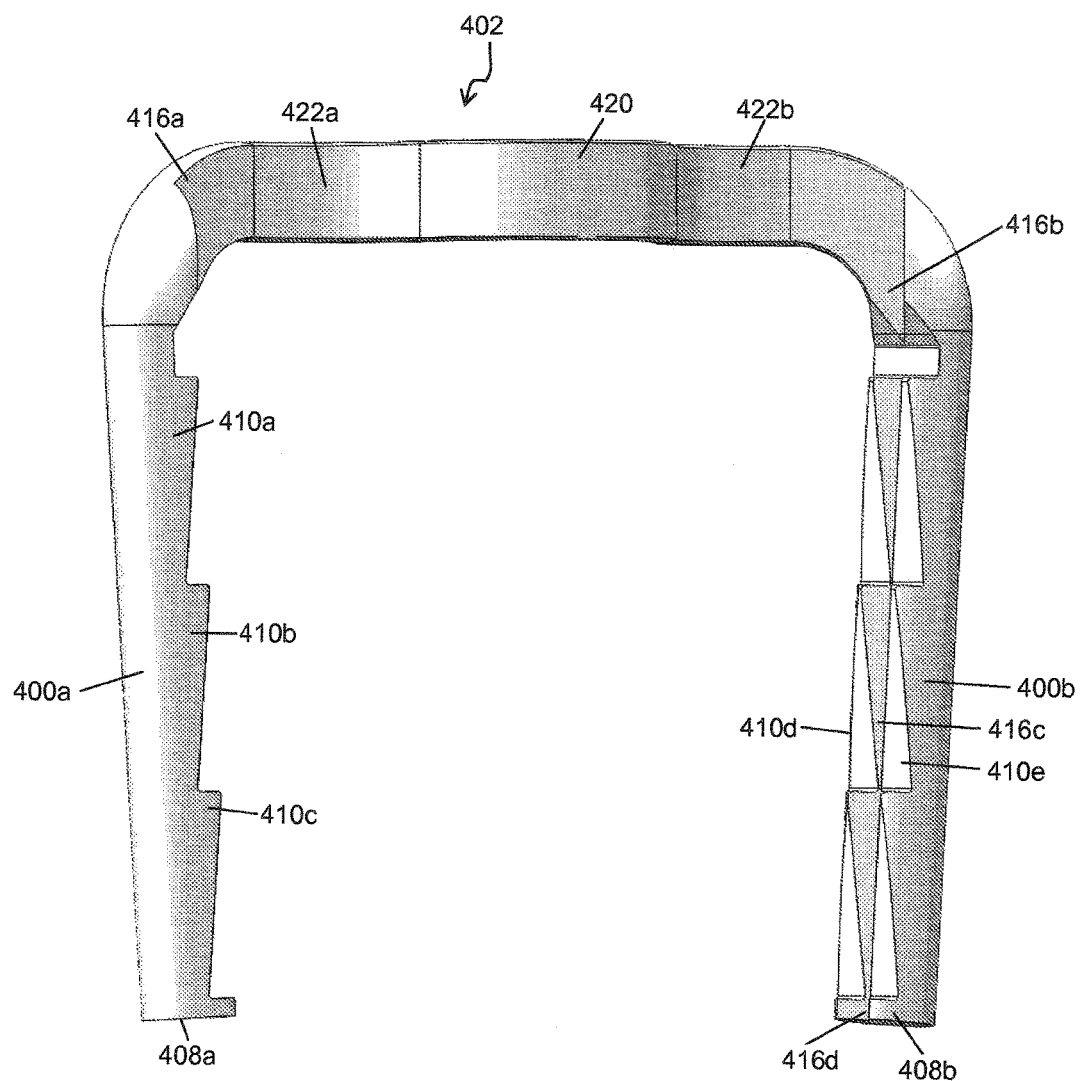
FIG. 4 is a side angled view of a compression staple.

FIG. 4 is a side angled view of a compression staple. The compression staple may have a bridge 402 connecting two or more legs 400a, 400b.

The bridge 402 may be curved in a lateral direction. For example, the side profile of a bridge may be relatively flat, while the bridge may curve in the x-y plane. For example, the bridge may have a central curved portion 420 and peripheral curved portions 422a, 422b. The bridge may be gull-wing shaped. The bridge may have three or more curves.

The legs 400a, 400b may each have a foot 408a, 408b at the distal ends of the legs. The legs may include one or more surface features 410a, 410b, 410c. Grooves 416a, 416b may run along the length of the legs. In some embodiments, portions of the groove 416c may come between portions of the surface features 410d, 410e. In some embodiments, the groove may be sufficiently deep so that the surface features form separate columns 410d, 410e. Portions of the groove 416d may also come between portions of the foot 408b.

Figure 5:
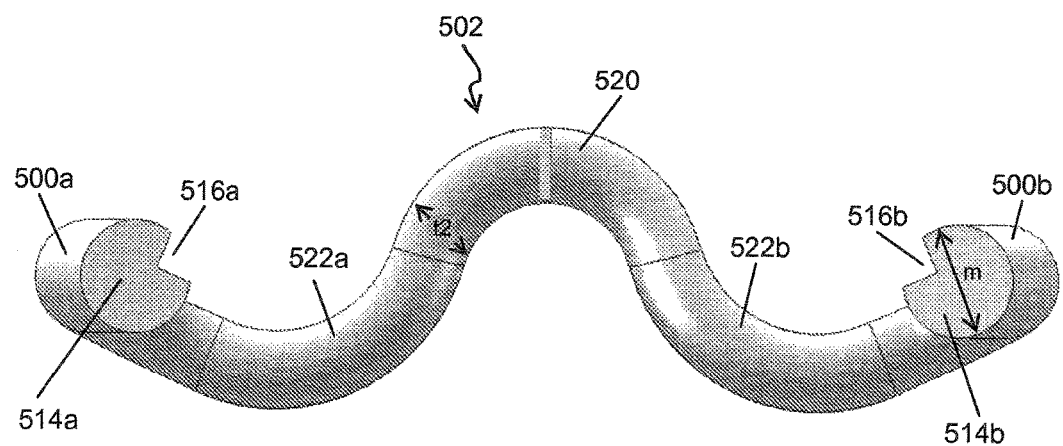
FIG. 5 is a bottom view of a compression staple.

FIG. 5 is a bottom view of a compression staple. Two or more legs 500a, 500b may be adjoined by a bridge 502.

The bridge 502 may have a curved shape. For example, the bridge may have gull-wing shaped curves. The bridge may have three or more curves, such as a central curve 520 and peripheral curves 522a, 522b. The bridge may be symmetrically shaped.

In some embodiments, the bridge may have a lateral thickness t2. The lateral thickness may remain substantially the same or may vary along the length of the bridge.

The legs 500a, 500b of the staple may have a groove 516a, 516b or channel extending therethrough. The groove or channel may extend along the entire length of the leg, or along a portion of the length of the leg. The groove may or may not be sufficiently deep to reach a center of a cross-section of a leg. The groove or channel may extend from an end portion of the bridge. The groove or channel may extend to a foot of a leg. The foot may have a flat bottom surface 514a, 514b, a rounded bottom surface, or any other surface as described elsewhere herein. The groove/channel may extend through the foot so that the foot has a cross-sectional shape that includes the groove/channel. For example, a wedge shaped groove may yield a cloven foot. The foot cross-section may include a circular cross-section with a pie shaped wedge removed. The wedge may or may not reach to the center of the cross-section of the leg and/or foot.

A foot may have a dimension m (e.g., length, width, diagonal, diameter). In some embodiments, the dimension of the foot m may be greater than the lateral thickness of the bridge t2. In some embodiments, the foot dimension may be greater than the lateral thickness of the bridge due to the dimension of the groove.

Figure 6:
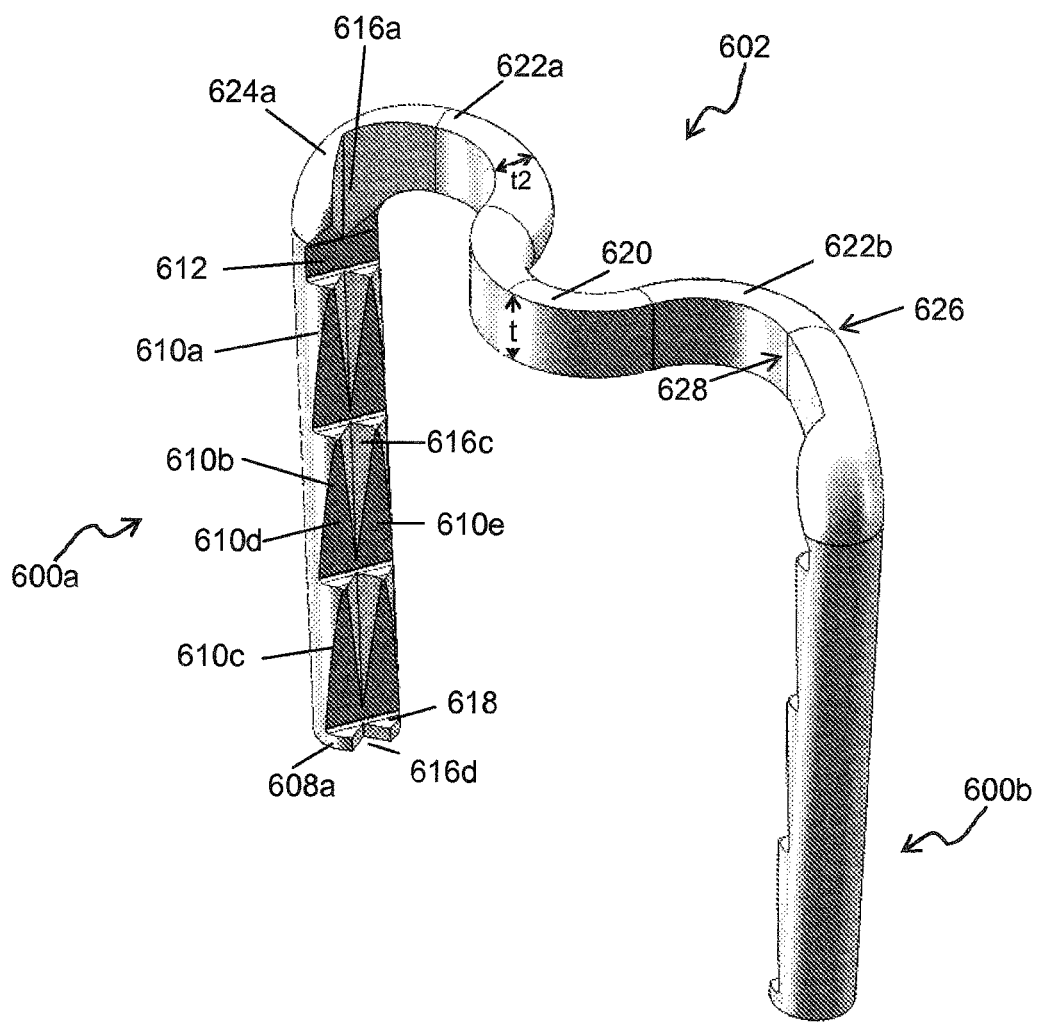
FIG. 6 is an upper perspective view of a compression staple in accordance with an embodiment of the invention.

FIG. 6 is an upper perspective view of a compression staple in accordance with an embodiment of the invention. A bridge 602 may connect two or more legs 600a, 600b.

The bridge 602 may include a plurality of curved portions. In some embodiments, the bridge may include three or more curved portions. For example, the bridge may include a central curve 620 and two or more peripheral curves 622a, 622b. The bridge may have a gull-wing shape. The bridge may have a vertical thickness t and a lateral thickness t2. In some embodiments, the vertical thickness t (i.e. bridge height) may be greater than, less than, or about equal to the lateral thickness t2 (i.e. bridge thickness).

The bridge may have a first side 626 and a second opposing side 628. In some embodiments, the first side may be rounded while the second side is flat. Alternatively, both the first and second sides may be rounded or flat. In some instances, the flat side may be a carveout of the bridge matching the contour of one or more groove along the legs of the staple. In some embodiments, the sides of the bridge may be non-symmetrical (e.g., flat side and rounded side). In various embodiments, the non-symmetry may lead to the bridge height being greater than the bridge width. In various embodiments, the ratio of the bridge height to width provides for increased spring strength compared to the weight of material in the bridge. This may cause less material to be used while maintaining a desired compressive force by the staple. For example, less material may be used while the bridge may be capable of delivering 30-40 lbs, or any other force measurement described herein, when delivered. Using less material may save in material costs and/or may cause the staple to weigh less. This may reduce certain undesirable effects experienced by the recipient. Having a portion of the staple bridge cut away may result in the bridge being taller than it is thick (e.g., t>t2). The vertical thickness t may permit the staple to provide a sufficient compressive force.

In some embodiments, the height may permit the legs to provide a sufficient force. The cut away, reducing the lateral thickness may permit the bridge to stretch. Shaving a side of the bridge, such as a front or back side of the bridge, reducing lateral thickness t2 may permit the bridge to act resiliently. The bridge may stretch with greater ease or resiliency if t2 has a lower value than t.

The legs 600a, 600b may extend from the bridge. The legs may or may not be parallel to one another. In some embodiments, in a relaxed state, the legs are convergent at the tips toward one another. The legs may include surface features 610a, 610b, 610c. As previously described, the surface features may include teeth, ramps, barbs, or serrations. In some embodiments, a portion of a leg does not have surface features 612.

A groove 616a may extend through the leg 600a. The groove may have any shape. In some embodiments, the groove may be wedge-shaped. An upper part of the groove 616a may form a wedge at an end of the bridge 624a. Middle portions of the groove 616c may form wedges through the surface features 610b. The groove may divide a surface feature into two protruding parts 610d, 610e. In some embodiments, one groove is provided per leg. In alternate embodiments, a plurality of grooves are provided per leg. A plurality of grooves may divide surface features of the legs into any number of portions. For examples, the grooves may divide the surface features into any number of columns along the length of the leg. The grooves may be dimensioned or shaped to match a staple delivery mechanism. A portion of a staple delivery mechanism may rest in the groove and/or grooves. A groove may have a lower portion 616d that may form a wedge through a foot 608a of the staple. The foot may form a ledge with a top surface 618 which may or may not be continuous due to the groove.

The bridge may have a flat side 628 which may be a side of the bridge facing the groove 616a. The flat side of the bridge may meet the contour of a side of the groove. A rounded side 626 of the bridge may meet the contour of a rounded side of a leg.

FIG. 7 is a lower perspective view of a compression staple provided in accordance with an embodiment of the invention. The staple may include two legs 700a, 700b extending from a bridge 702. The legs may include surface features 710a, 710b, 710c, such as teeth, ramps, barbs, or serrations. A groove 716a, 716b may extend along the length of a leg. The groove may be on the inner portions of the legs facing one another. As previously mentioned, the groove may have any shape. For example, the groove may form a flat bottomed channel. The groove may have any cross-sectional shape, such as a curved shape, semi-circular shape, wedge shape, rectangular shape, trapezoidal shape, or any other shape. The groove may pass through an end of the bridge 724a, the surface features 710a, 710b, 710c, and a foot 708a of the leg.

The bridge 702 may have a rounded side 726 and a flat side 728. The flat side of the bridge may match up or line up with a side of the groove 716a.

A compression staple may be prepared for delivery to a target, and delivered to the target. In some embodiments, the target may include bone tissue or fragments. The compression staple may be a bone staple used to connect multiple bone fragments. The compression staple may be prepared for delivery to a target by being loaded into a staple delivery mechanism. The compression staple may or may not have had a pre-loaded configuration before being loaded into the staple delivery mechanism. The staple delivery mechanism may deliver the staple to the target. In some embodiments, after the staple has been delivered to the target, the staple may reach a delivered equilibrium state.

The compression staple may be prepared for delivery to a target by being loaded into a staple delivery mechanism. In some examples, the staple delivery mechanism may be a staple gun. For example, the staple delivery mechanism may have one or more features or characteristics of a delivery mechanism provided in U.S. Pat. No. 6,783,531, which is hereby incorporated by reference in its entirety.

In some embodiments, the staple may be pre-loaded in a prepared state prior to be being loaded into the staple delivery mechanism. In some embodiments, the pre-loaded staples may be packaged and/or shipped. The staple may be pre-loaded at the point of manufacture and/or prior to shipping and/or distribution. In some embodiments, a loading mechanism, such as those described elsewhere herein, may be used to pre-load a staple. Pre-loading a staple may include tensioning a staple to a desired delivery state. Pre-loading a staple may include getting it into a state from which it can be delivered via a staple delivery mechanism. For example, pre-loading a staple may include stretching a bridge of the staple and/or torquing the legs of the staple relative to its relaxed state.

Alternatively, the staples need not be pre-loaded prior to distribution, and may be loaded after distribution. The staples may be loaded at a staple delivery site. In some embodiments, the staples may be loaded via a separate loading mechanism and then transferred to a delivery mechanism, or the staples may be loaded using the staple delivery mechanism.

In some embodiments, loading a staple may include tensioning one or more portions of the staple from its relaxed state. For example, if a staple has a relaxed state as shown in FIG. 1, loading the staple may include causing the angle $\theta$ of the legs to vary. Loading the staple may also include causing the width w of the staple to vary. For example, in a relaxed state, the legs may be angled inward, so that they are converging toward one another. Loading the staple may reduce the inward angle $\theta$ or may cause the legs to become parallel (e.g., $\theta$ equals 0). In some instances, during the loading of the staple, the legs may be splayed outward (e.g., $\theta$ may have a negative value). After the staple has been loaded, the legs may reach a parallel configuration, or any other angled (inward or outward) configuration. The reduction of the angle (e.g., moving the legs outward from their relaxed state) may cause the legs to provide a clamping or compressive force on bone tissue at or near the ends of the legs. In some embodiments, throughout the loading process, the angle may change a small amount. For example, the angle change may be less than, greater than, or equal to about 1 degree, 2 degrees, 3 degrees, 4 degrees, 5 degrees, 6 degrees, 7 degrees, 8 degrees, 9 degrees, 10 degrees, 12 degrees, 15 degrees, 20 degrees, or 25 degrees.

Loading the staple may also include causing the width of the staple to vary. For example, in a relaxed state, the staple may have a width w. When the staple has been loaded, the bridge of the staple may be stretched, so that the staple width is greater than the width in the relaxed state. This may permit the staple to provide a compressive force at or near the bridge of the staple. This may also permit the staple to provide a compressive force at the legs of the staple near the proximal end of the staple. In some embodiments, throughout the loading process, the width may change by a small amount. For example, the width may increase by less than, greater than, or equal to about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.7 mm, or 2 mm.

Various loading mechanisms may be used to take a staple in its relaxed state and load it into a delivery state. Some examples of loading mechanisms are provided below. Alternative loading mechanisms may be used to load a staple.

FIG. 8 provides an example of a method of preparing a compression staple for delivery to a target in accordance with an embodiment of the invention. A ramp loading mechanism may be used to load or pre-load the staple. The ramp loading mechanism may be used to take a staple in its relaxed state and put it into a delivery state ready to be delivered via a staple delivery mechanism. The ramp loading mechanism may be a pre-loading mechanism or may be the staple delivery mechanism. The ramp loading mechanism may approach a staple from the distal ends of the legs to prepare the staple for a delivery state.

Figure 8A:
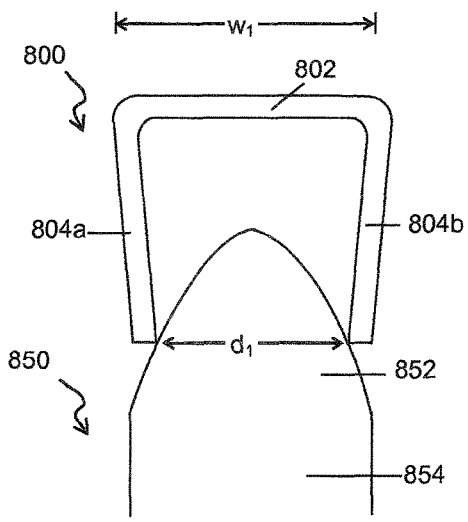
FIG. 8A shows contact between a ramp loading mechanism and the ends of the legs of the compression staple.

FIG. 8A shows contact between a ramp loading mechanism and the ends of the legs of the compression staple. The compression staple 800 may be in a relaxed state. The compression state may have a bridge 802 providing the staple with a width $w_1$, and legs 804a, 804b extending from the ends of the bridge. The legs may be arranged to converge slightly inward toward one another in the relaxed state. The distal ends of the legs may be a distance $d_1$ apart. In some embodiments, in a relaxed state, $w_1$ may be greater than $d_1$.

The ramp loading mechanism 850 may have a ramp section 852 and a parallel section 854. The ramp loading mechanism may approach the staple 800 from the distal ends of the legs 804a, 804b of the staple so that the distal ends of the staple legs contact the ramp first. In some embodiments, one or more portion of the loading mechanism may engage with one or more grooves of the staple legs. The grooves may be on the inner surfaces of the legs of the staple.

Figure 8B:
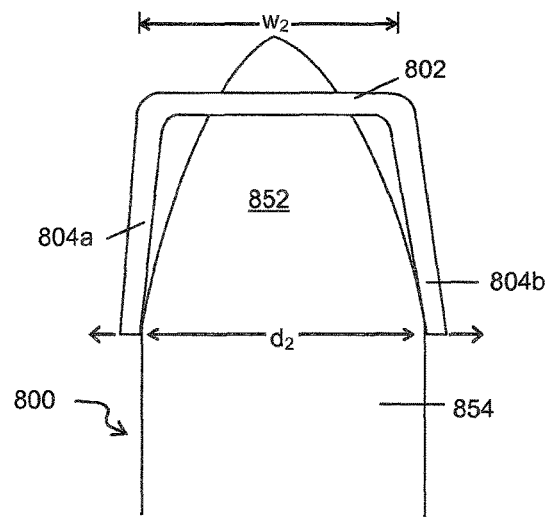
FIG. 8B shows further contact between the ramp, thereby causing the legs of the compression staple to splay outward.

FIG. 8B shows further contact between the ramp, thereby causing the legs of the compression staple to splay outward. The ramp loading mechanism 850 and/or staple 800 may be pushed toward one another, so that the ramp loading mechanism forces the legs of the staple apart. The ramp loading mechanism may have a width that is greater than $d_1$. As a ramp section 852 of the ramp loading mechanism is pushed toward the bridge of the staple, the legs of the staple may be torqued outwardly, so that the distance between the distal ends of the legs is now $d_2$ which has a greater value than $d_1$. Force may be exerted at the distal ends of the legs where the ramp is forcing the legs apart.

The bridge 802 of the staple may have a width $w_2$ which may be substantially the same as $w_1$. The legs may be torqued outwardly prior to significant stretching in the bridge. In some embodiments, one or more portion of the loading mechanism may be sliding along grooves of the leg.

Figure 8C:
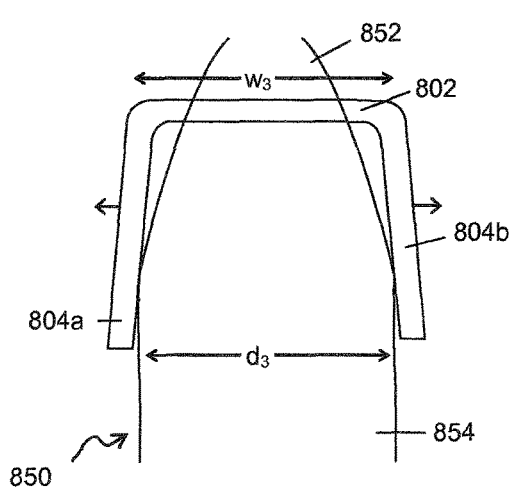
FIG. 8C shows contact between the ramp and a portion of the legs closer to the bridge of the compression staple.

FIG. 8C shows contact between the ramp and a portion of the legs closer to the bridge of the compression staple. The ramp loading mechanism 850 and the staple 800 may be pushed further toward one another, causing the widest portion of the ramp section 852 to contact the legs 804a, 804b of the staple, closer toward the bridge 802 of the staple. Force may be exerted along the contact point at the legs where the ramp is forcing the legs apart. The legs of the staple may still be torque outward, so that that the distance between the distal ends of the legs is now $d_3$ which may have a greater value than $d_1$. The distance between the legs $d_3$ may or may not have a greater value than $d_2$.

The bridge 802 of the staple may have a width $w_3$. In some embodiments, as the ramp moves upward toward the bridge, the bridge may begin stretching. A curved shape of the bridge may provide the bridge with the flexibility to stretch. The bridge may be stretched partway so that the width $w_3$ may be greater than $w_1$. The legs may still be torqued outwardly as the stretching in the bridge begins.

Figure 8D:
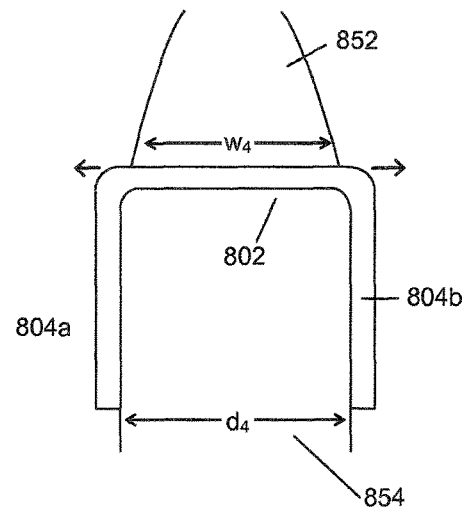
FIG. 8D shows a delivery ramp mechanism that has caused the compression staple to expand at the bridge in preparation for delivery.

FIG. 8D shows a delivery ramp mechanism that has caused the compression staple to expand at the bridge in preparation for delivery. The staple 800 may now be at the parallel section 854 of the ramp loading mechanism 850. The legs 804a, 804b of the staple may contact the parallel sections of the ramp loading mechanism. Force may be exerted along the bridge 802 and legs of the staple. The staple may be at a delivery state with a stretched bridge, and legs that are slightly torqued to be in a parallel configuration. The distal ends of the legs may have a distance of $d_4$ which may have a greater value than $d_1$. In some embodiments, $d_4$ may have a greater value than $d_2$, and a lesser value than $d_3$.

The bridge 802 of the staple may have a width $w_4$. The bridge may be stretched so that the width $w_4$ may be greater than $w_1$. The value of $w_4$ may be greater than $w_3$. In some embodiments, $w_4$ may be substantially the same as $d_4$, indicating the legs are in a substantially parallel configuration. In some embodiments, it may be desirable for a staple to have a parallel-legs configuration in a delivery state. In alternate embodiments, the legs may have different configurations in a delivery state, and the section 854 of the ramp loading mechanism may be shaped accordingly. A compression force may be provided at the bridge of the staple and along the legs of the staple. In some embodiments, a loading mechanism may be engaged with grooves in inner surfaces of the legs of the staple to hold the staple in the delivery state.

FIG. 9 provides another example of a method of preparing a compression staple for delivery to a target. An expanding loading mechanism may be used to load or pre-load the staple. The expanding loading mechanism may be used to take a staple in its relaxed state and put it into a delivery state ready to be delivered via a staple delivery mechanism. The expanding loading mechanism may be a pre-loading mechanism or may be the staple delivery mechanism. The expanding loading mechanism may expand outward from between the legs to prepare the staple for a delivery state.

FIG. 9A shows contact between an expanding loading mechanism and the ends of the legs of the compression staple. The compression staple 900 may be in a relaxed state. The compression state may have a bridge 902 providing the staple with a width $w_1$, and legs 904a, 904b extending from the ends of the bridge. The legs may be arranged to converge slightly inward toward one another in the relaxed state. The distal ends of the legs may be a distance $d_1$ apart. In some embodiments, in a relaxed state, $w_1$ may be greater than $d_1$.

The expanding loading mechanism 950 may be located between the legs of the staple 900. The expanding loading mechanism may have parallel sides so that the distal ends of the staple legs contact the ramp first. In some embodiments, the expanding loading mechanism may contact the grooves of the staple legs. The grooves may be provided on the inner surface of the staple legs.

FIG. 9B shows further expansion of the expanding loading mechanism, thereby causing the legs of the compression staple to torque slightly outward. The sides of the expanding loading mechanism 950 may expand outward, pushing against the legs 904a, 904b of the staple 900, so that the expanding loading mechanism forces the legs of the staple apart. At this point, the expanding loading mechanism may have a width that is greater than $d_1$. The legs of the staple may be torqued outwardly, so that the distance between the distal ends of the legs is now $d_2$ which has a greater value than $d_1$. Force may be exerted at the distal ends of the legs where the expanding loading mechanism is forcing the legs apart. In some embodiments, the expanding loading mechanism may be fitting into the grooves of the legs to force them apart.

The bridge 902 of the staple may have a width $w_2$ which may be substantially the same as $w_r$. The legs may be torqued outwardly from their relaxed state prior to significant stretching in the bridge.

FIG. 9C shows contact between the expanding loading mechanism and the ends of the bridge of the compression staple. The sides of the expanding loading mechanism 950 may expand further outward and may reach the end of the bridge 902 of the staple 900, causing the sides to contact the sides of the legs 904a, 904b of the staple, and the ends of the bridge 902 of the staple. Force may be exerted along the length of the legs where the expanding loading mechanism is forcing the legs apart. The legs of the staple may still be torque outward relative to their relaxed state, so that that the distance between the distal ends of the legs is now $d_3$ which may have a greater value than $d_1$. The distance between the legs $d_3$ may have a greater value than $d_2$. If the desired delivery state of the staple is with parallel legs, the sides of the expanding loading mechanism may be parallel, and the legs may be torque to a parallel state.

The bridge 902 of the staple may have a width $w_3$. At this point the bridge may not yet be substantially stretched, so that width $w_3$ may be substantially the same as $w_1$. The legs may be torqued without yet substantially stretching the bridge.

FIG. 9D shows an expanding loading mechanism that has caused the compression staple to expand at the bridge in preparation for delivery. The sides of the expanding loading mechanism 950 may have expanded further so that the bridge 902 of the staple has been stretched and the sides of the legs 904a, 904b of the staple may contact the sides of the expanding loading mechanism. Force may be exerted along the bridge and legs of the staple. The staple may be at a delivery state with a stretched bridge, and legs that are slightly torqued to be in a parallel configuration. The distal ends of the legs may have a distance of $d_4$ which may have a greater value than $d_1$. In some embodiments, $d_4$ may have a greater value than $d_2$ and $d_3$.

The bridge 802 of the staple may have a width $w_4$. The bridge may be stretched so that the width $w_4$ may be greater than $w_1$. In some embodiments, $w_4$ may be substantially the same as $d_4$, indicating the legs are in a substantially parallel configuration. In some embodiments, it may be desirable for a staple to have a parallel-legs configuration in a delivery state. In alternate embodiments, the legs may have different configurations in a delivery state, and the sides of the expanding loading mechanism may be shaped accordingly. A compression force may be provided at the bridge of the staple and along the legs of the staple. In some embodiments, a loading mechanism may be engaged with grooves in inner surfaces of the legs of the staple to hold the staple in the delivery state.

FIG. 10 illustrates an additional exemplary method of preparing a compression staple for delivery to a target. A rear loading mechanism may be used to load or pre-load the staple. The rear loading mechanism may be used to take a staple in its relaxed state and put it into a delivery state ready to be delivered via a staple delivery mechanism. The rear loading mechanism may be a pre-loading mechanism or may be the staple delivery mechanism. The rear loading mechanism may approach a staple from the bridge side to prepare the staple for a delivery state.

Figure 10A:
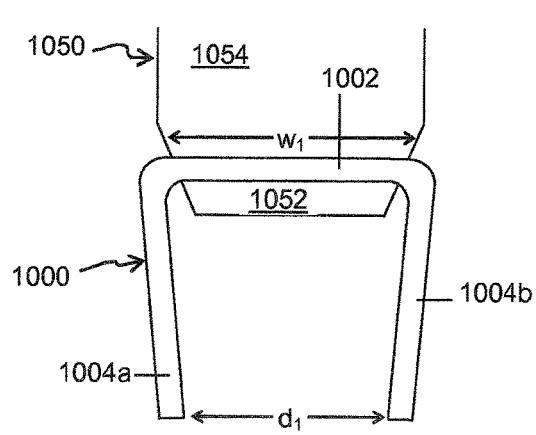
FIG. 10A shows contact between a rear loading mechanism and the ends of the bridge of the compression staple, at or near the proximal ends of the legs staple.

FIG. 10A shows contact between a rear loading mechanism and the ends of the bridge of the compression staple, at or near the proximal ends of the legs staple. The compression staple 1000 may be in a relaxed state. The compression state may have a bridge 1002 providing the staple with a width $w_1$, and legs 1004a, 1004b extending from the ends of the bridge. The legs may be arranged to converge slightly inward toward one another in the relaxed state. The distal ends of the legs may be a distance $d_1$ apart. In some embodiments, in a relaxed state, $w_1$ may be greater than $d_1$.

The rear loading mechanism 1050 may have a ramp section 1052 and a parallel section 1054. The rear loading mechanism may approach the staple 1000 from the bridge side of the staple so that the proximal ends of the staple legs 1004a, 1004b contact the ramp section first. In some embodiments, the rear loading mechanism may have portions that may engage with grooves of the staples. The rear-loading mechanism may interface with grooves on inner surfaces of the staple legs, starting from the proximal ends of the staple legs, which meet the ends of the bridge.

Figure 10B:
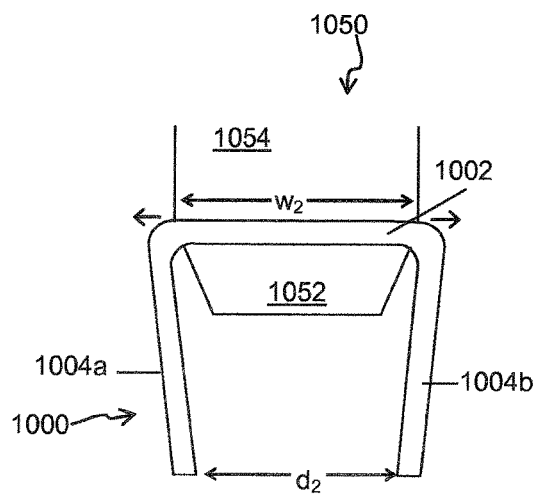
FIG. 10B shows further contact between the rear loading mechanism and the staple, thereby causing the bridge to expand.

FIG. 10B shows further contact between the rear loading mechanism and the staple, thereby causing the bridge to expand. The rear loading mechanism 1050 and/or staple 1000 may be pushed toward one another, so that the rear loading mechanism forces the bridge 1002 of the staple to stretch. The rear loading mechanism may have a width that is greater than $w_1$. As a ramp section 1052 of the rear loading mechanism is pushed toward the bridge of the staple, from the rear of the staple, causing the bridge to stretch, so that the width of the staple is now $w_2$ which has a greater value than $w_1$. Force may be exerted at the proximal ends of the legs where the ramp section is forcing the bridge to stretch. The rear loading mechanism may slide along the grooves of the staple legs.

The legs 1004a, 1004b of the staple may distal ends that are a distance $d_2$ apart which may or may not be greater than $d_1$. The bridge may be stretched prior to any substantial torquing of the legs.

Figure 10C:
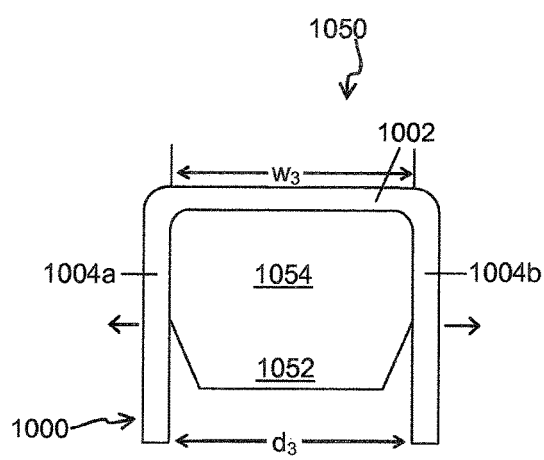
FIG. 10C shows a rear loading mechanism that has caused the compression staple to expand at the bridge and the legs to torque outward from their relaxed state in preparation for delivery.

FIG. 10C shows a rear loading mechanism that has caused the compression staple to expand at the bridge and the legs to torque outward from their relaxed state in preparation for delivery. The staple 1000 may now be at the parallel section 1054 of the rear loading mechanism 1050. In some embodiments, only a portion of the legs 1004a, 1004b of the staple have reached the parallel section of the rear loading mechanism. For example, greater than, less than, or equal to about 1 mm, 2 mm, 3 mm, 4 mm, or 5 mm of the proximal ends of the staple legs have reached the parallel section. Alternatively, the entirety of the length of the legs of the staple have reached the parallel section. Force may be exerted along the bridge 1002 and legs of the staple. The staple may be at a delivery state with a stretched bridge, and legs that are slightly torqued to be in a parallel configuration. The distal ends of the legs may have a distance of $d_3$ which may have a greater value than $d_1$ and $d_2$.

The bridge 1002 of the staple may have a width $w_3$. The bridge may be stretched so that the width $w_3$ may be greater than $w_1$. In some embodiments, $w_3$ may be substantially the same as $d_3$, indicating the legs are in a substantially parallel configuration. In some embodiments, it may be desirable for a staple to have a parallel-legs configuration in a delivery state. In alternate embodiments, the legs may have different configurations in a delivery state, and the section 1054 of the rear loading mechanism may be shaped accordingly. A compression force may be provided at the bridge of the staple and along the legs of the staple. In some embodiments, a loading mechanism may be engaged with grooves in inner surfaces of the legs of the staple to hold the staple in the delivery state.

An advantage of using a rear loading mechanism is that is need not cause the legs to torque further than its delivery state. Similarly, an expanding loading mechanism may also not cause the legs to torque further than its delivery state. For example, if the legs are to be parallel in their delivery state, the legs need not be torqued past a parallel configuration (e.g., the legs are not splayed outward past a parallel configuration). This may reduce wear on the staple material, in comparison to a loading mechanism that causes the legs to splay outward first, prior to reaching a parallel delivery state.

In some embodiments, a rear loading mechanism may be loaded quickly. For example, the ramp portion of the rear loading mechanism may be jammed quickly into the staple to stretch the bridge. A percussive force may be used to cause the rear loading mechanism to stretch the bridge of the staple. For example, the rear loading mechanism may be pushed into the rear of the staple.

FIG. 11 provides an example of states of a compression staple as it is delivered to a target. As previously described, a staple may have a relaxed state. The staple may then be loaded using a loading mechanism, such as those described elsewhere herein. The staple may be loaded into a delivery state, ready for delivery to a target. The loading mechanism may be part of a staple delivery mechanism, or may be used to pre-load the staple. The staple may have a delivery state when it is delivered to the target. After the staple has been delivered to a target, it may reach an equilibrium state.

Figure 11A:
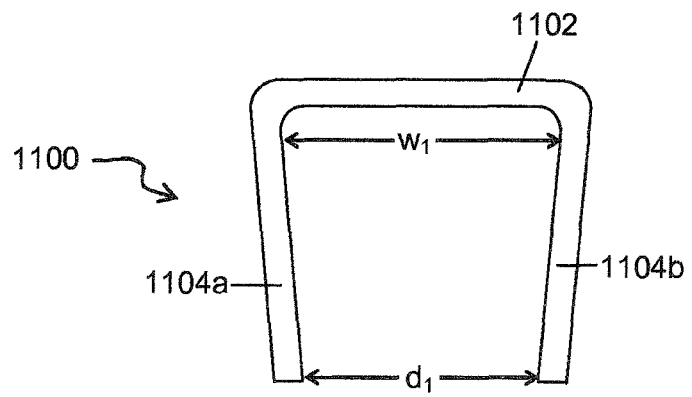
FIG. 11A shows a relaxed state of a staple.

FIG. 11A shows a relaxed state of a staple 1100. The staple may have a bridge 1102 connecting two or more legs 1104a, 1104b. The staple may include any features or characteristics as described elsewhere herein. The staple may have a width $w_1$. The distal ends of the staple legs may be a distance $d_1$ apart. In some embodiments, in a relaxed state, the legs may be naturally converging inwards (e.g., $d_1 < w_1$). In alternate embodiments, the legs may have a substantially parallel configuration or may be splayed outwards in their relaxed state.

Figure 11B:
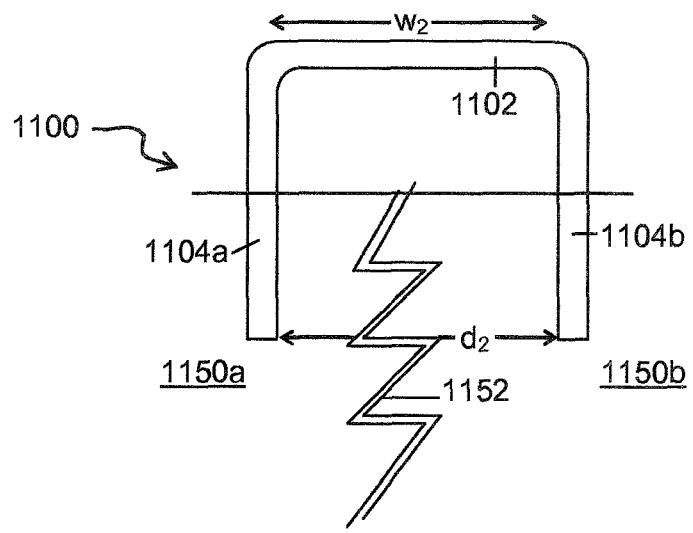
FIG. 11B shows a delivery state of a staple.

FIG. 11B shows a delivery state of a staple 1100. In a delivery state, the bridge 1102 of the staple may be stretched. In some embodiments, the bridge may be formed of a flexible material that may enable the stretching of the bridge. The bridge may also be shaped with one or more curve or bend that may provide flexibility, and enable stretching of the staple. For example, the bridge may have a gull-wing shape that may permit stretching of the bridge, thereby increasing the width of the staple. In the delivery state, the staple may have a width $w_2$ which may be greater than the staple width $w_1$ in the relaxed state. A compression force may be provided by the bridge that has been stretched in its delivery state.

In the delivery state, the legs 1104, 1104b may be torqued. For example, in a relaxed state, the legs may angle inward toward one another. In a delivery state, the legs may have a substantially parallel configuration. In alternative embodiments, the legs may be angled slightly outward or inward, but may be torque outward relative to the relaxed state. The distal ends of the staple legs may be a distance $d_2$ apart in the delivery state, which may be greater than the distance $d_1$ apart in the relaxed state. Furthermore, in some embodiments, the difference in the distances of the distal ends of the legs may be greater than the stretch of the bridge (e.g., $d_2 - d_1$ may be greater than $w_2 - w_1$). In one example, the bridge may stretch by about 1 mm (e.g., $w_2 - w_1$). The legs may be torqued apart by about 1 mm to get them into a parallel configuration, and the change in bridge length may also cause the distance between the legs to increase an additional 1 mm (e.g., $d_2 - d_1 = 2$ mm). A compression force may be provided by the legs that have been torque in their delivery state. The slight torquing of the legs may cause a slight pinching by the legs of staple.

In some embodiments, a method of loading and/or delivering the staple may also include determining the delivery state of the flexible. This may include determining the bridge length (and/or stretch) and/or leg torque/angle. The determination of bridge length and leg position may depend on a desired degree and/or distribution of compressive force to be delivered to a target. For example, a selected force magnitude and/or direction to be delivered to connect bone fragments may be determined. Based on said determination, the degree of stretch and/or angle of legs upon delivery may be determined. A staple loading and/or delivery mechanism may be selected or adjusted to provide the desired staple delivery configuration. For example, if a greater degree of compressive force is required, then a wider staple loading and/or delivery mechanism may be selected (causing greater stretch/tension in the staple), or a staple loading and/or delivery mechanism may be adjusted to provide a wider configuration. If a greater degree of compressive force is desired deeper in the bone than at the surface of the bone, the legs may be torqued outward more at the outset of the delivery state, and an appropriate loading and/or delivery mechanism may be selected and/or adjusted. The degree of bridge stretch and/or leg torque of the staple may depend on the desired compression force distribution profile along the depth of the bone fragments to be connected. The staple may be loaded into the selected or adjusted loading and/or delivery mechanism. The staple may then be delivered in its selected delivery state.

The staple 1100 may be delivered while in its delivery state. The staple may be delivered via a staple delivery mechanism, such as a staple gun. The staple may be delivered to a target, such as bone. The staple may be used to connect a plurality of bone fragments 1150a, 1150b. In some embodiments, a fracture 1152 may be provided between bone fragments. The staple may be delivered so that a first leg 1104a of a staple goes into a first bone fragment 1150a and a second leg 1104b of a staple goes into a second bone fragment 1150b. The staple may connect the separate bone fragments.

The extent to which the staple legs are separated in a delivery state can be varied in embodiments of the invention. The induced compressive forces between the legs may be proportional to the amount of displacement of the legs as the bowed portion is moved through range of motion in which elastic behavior is exhibited. In this regard it should be evident that herein lies one of the advantages of the present invention, i.e. the capability of selecting the optimal compressive force for an application by spreading apart the staple legs by a predetermined amount. For example, spreading the staple apart further (e.g., at the bridge and/or at the legs) may yield a greater compressive force. Upon insertion into bone, the embedded staple legs will cause the opposing bone faces to be pressed into each other with a predetermined amount of force.

The staple legs may have grooves. The grooves may extend along the length of the staple legs. In some embodiments, the grooves may be on the inner surface of the staple legs that are facing one another. The grooves may be configured to engage with one or more guiding member of a staple delivery mechanism and/or loading mechanism. For example, a staple delivery mechanism, such as a staple gun, may be used to deliver a staple to a target. The staple delivery mechanism and/or loading mechanism may have one or more guiding feature that may permit desired placement of the staple. For example, the staple delivery mechanism and/or the loading mechanism may have a first guide and a second guide. A groove of a first leg of the staple may be configured to accept and/or interface with the first guide of the staple delivery mechanism, and a groove of the second leg of the staple may be configured to accept and/or interface with the second guide of the staple delivery mechanism. The guides of the staple delivery mechanism and/or loading mechanism may hold the staple in tension at a delivery state. The guides may rest in the grooves of the staple and cause the staple to be stretched in its delivery state. A staple delivery mechanism may include a trigger mechanism or actuating mechanism that may cause the staple to be delivered to a target region, such as bone tissue, off the guides.

In some embodiments, holes may be drilled into bone fragments prior to the delivery of the staple. For example, holes may be provided (via drilling, boring, or any other mechanism known in the art) into which the legs of the staples may be inserted. In some embodiments, the ends of the legs of the staples may have any shapes when inserted into the holes. For example, the feet of the staples may be flat, rounded, sharpened, or have any other shape or combination thereof. In other embodiments, holes need not be drilled into the bone fragments prior to delivery. The staples may be driven into the bone tissue. In some embodiments, the staples may have sharpened feet, or sharpened feet with rounded edges to assist with driving the staples into the tissue. The staples may be driven in with a percussive force.

Figure 11C:
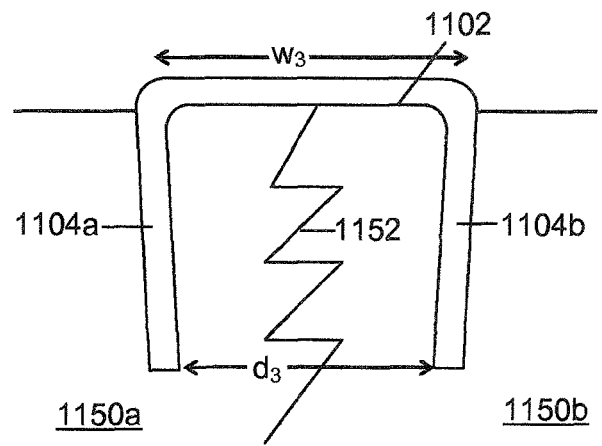
FIG. 11C shows an equilibrium state of the staple.

FIG. 11C shows an equilibrium state of the staple. After a staple has been delivered to a target, such as bone tissue, the staple may reach an equilibrium state. In some embodiments, the staple may reach an equilibrium state after some time has elapsed. In some embodiments, the bone fragments 1150a, 1150b may be brought closer together, and the fracture 1152 may be tightly held together, due to the compressive forces provided by the staple 1100. As the bone fragments may be brought tighter together, the staple width may decrease a little bit over time. In some embodiments, the staple legs may bend slightly inward toward their relaxed state. Alternatively, the staple legs may remain in a parallel configuration. For example, the staple bridge 1102 may be less stretched as the bone gathers together. The staple may have a width $w_3$ which may be less than $w_2$. In some embodiments, the equilibrium width $w_3$ may be greater than or equal to $w_1$. The staple legs 1104a, 1104b may have distal ends that are a distance $d_3$ apart. The distance $d_3$ may be less than $d_2$. In some embodiments, the equilibrium distance $d_3$ may be greater than or equal to $d_1$.

In various embodiments, the distance between the tensioned state of the legs and the untensioned state of the legs at the foot of the legs may be less than, greater than, or equal to about 2.5 mm, 2 mm, 1.5 mm, 1 mm, or 0.5 mm. In various embodiments, the distance is less than about 1 mm. The distance between the tensioned and untensioned legs may be reflected in the distance the legs travel over time upon insertion into bone (e.g., between a delivery state and equilibrium state, $d_2-d_3$). In other embodiments, the distance between the tensioned and untensioned legs may be reflected in the change in distance between the relaxed state and the delivery state (e.g., $d_2-d_1$). In a preferable embodiment, the staple legs travel less than, greater than, or equal to about 2.5 mm, 2 mm, 1.5 mm, 1 mm, or 0.5 mm over time while providing compression of bone segments.

After the staple has been delivered to a target area, it may be flush with the bone surface. The underside of the bridge of the staple may or may not contact the bone surface. The legs may be straight. The legs may remain straight or may be curved or bent over time.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A compression staple comprising:
a bridge having a first end, a second end, and an elongate body with one or more curves between the first end and the second end;
a first leg having a proximal end, a distal end, and an elongate body between the proximal end and the distal end, wherein the proximal end of the first leg is connected to the first end of the bridge, and wherein the first leg is solid in cross-section and has a first elongate groove on an exterior surface thereof, the first elongate groove extending along the elongate body of the first leg from the distal end of the first leg to the bridge and is partially defined by perimetric surfaces of the bridge, the first elongate groove configured to be contacted by a first guide on at least one of a staple loading mechanism and a delivery mechanism when the staple is loaded on one of the staple loading mechanism or the delivery mechanism in a tensioned state; and
a second leg having a proximal end, a distal end, and an elongate body between the proximal end and the distal end, wherein the proximal end of the second leg is connected to the second end of the bridge, and wherein the second leg is solid in cross-section and has a second elongate groove on an exterior surface thereof, the second elongate groove extending along the elongate body of the second leg from the distal end of the second leg to the bridge and is partially defined by perimetric surfaces of the bridge, the second elongate groove configured to be contacted by a second guide on at least one of the staple loading mechanism and the delivery mechanism when the staple is loaded on one of the staple loading mechanism or the delivery mechanism in the tensioned state,
wherein the staple is movable from a relaxed state to the tensioned state by spreading apart the first leg and the second leg from one another which lessens a curvature of the one or more curves of the elongate body of the bridge, the first leg and the second leg being resiliently urged toward one another when the staple is in the tensioned state.

2. The staple of claim 1 wherein the elongate body of the bridge is gull-wing shaped.

3. The staple of claim 1 wherein the first groove is provided along an inner surface of the first leg facing the second leg, and the second groove is provided along an inner surface of the second leg facing the first leg.

4. The staple of claim 1, wherein the staple is configured to achieve a force to staple width or force to staple height ratio of between about 25-45 lbs of compression force to 20 mm width or 20 mm height upon insertion into bone segments.

5. The staple of claim 4, wherein the amount of compression force upon insertion into bone segments varies by less than 80% along a length of the staple legs.

6. The staple of claim 1, wherein the one or more curves comprising a laterally curved shape, and wherein said bridge lies in a plane normal to axes of the staple legs.

7. The staple of claim 6, wherein the bridge forms a gull-wing shape, S-shape, Z-shape, or U-shape.

8. The staple of claim 1, wherein the first and second staple legs are moved apart by a distance of less than about 1 mm between the tensioned state and the relaxed state.

9. The staple of claim 1, wherein the staple legs have a flat base at the distal end of each of the first and second staple legs.

10. The staple of claim 1, wherein the staple legs contain at least one serrated barb.

11. The staple of claim 1, wherein the bridge includes a flat surface on one side such that a bridge height is greater than a bridge width.

12. The staple of claim 1, wherein the one or more curves of the bridge comprise at least three curves between the first end and second end.

13. The staple of claim 1, wherein the staple legs are moved apart by a distance of less than about 2 mm between the tensioned state and the relaxed state.

14. The staple of claim 1, further comprising:
a third groove on the exterior surface of the first leg, wherein the third groove is oriented substantially perpendicular to and intersects with the first elongate groove; and
a fourth groove on the exterior surface of the second leg, wherein the fourth groove is oriented substantially perpendicular to and intersects with the second elongate groove.

15. A compression staple comprising:
a bridge having a first end, a second end, and an elongate body with one or more curves between the first end and second end;
a first leg having a proximal end, a distal end, and an elongate body between the proximal end and the distal end, wherein the proximal end of the first leg is connected to the first end of the bridge, and wherein the first leg is solid in cross-section and has a first elongate groove on an exterior surface thereof, the first elongate groove being circumferentially open for an entire length thereof and extending along the first leg from the distal end of the first leg to the proximal end of the first leg, the first elongate groove extending along a side surface of the bridge to a top surface of the bridge; and
a second leg having a proximal end, a distal end, and an elongate body between the proximal end and the distal end, wherein the proximal end of the second leg is connected to the second end of the bridge, wherein the second leg is solid in cross-section and has a second elongate groove on an exterior surface thereof, the second elongate groove being circumferentially open for an entire length thereof and extending along the second leg from the distal end of the second leg to the proximal end of the second leg, the second elongate groove extending along the side surface of the bridge to the top surface of the bridge.

16. The staple of claim 15, wherein the one or more curves comprising a laterally curved shape, and wherein said bridge lies in a plane normal to axes of the staple legs.

17. The staple of claim 16, wherein the bridge forms a gull-wing shape, S-shape, Z-shape, or U-shape.

18. The staple of claim 15, further comprising:
a third groove on the exterior surface of the first leg, wherein the third groove is oriented substantially perpendicular to and intersects with the first elongate groove; and
a fourth groove on the exterior surface of the second leg, wherein the fourth groove is oriented substantially perpendicular to and intersects with the second elongate groove.

19. A compression staple comprising:
a bridge having a first end, a second end, and an elongate body with one or more curves between the first end and second end;
a first leg having a proximal end, a distal end, and an elongate body between the proximal end and the distal end, wherein the proximal end of the first leg is connected to the first end of the bridge, and wherein the first leg is solid in cross-section and has a first elongate groove on an exterior surface thereof, the first elongate groove extending an entire length of the elongate body from the distal end to the proximal end thereof, and wherein the first groove further extends into the first end of the bridge and is partially defined by perimetric surfaces of the bridge; and
a second leg having a proximal end, a distal end, and an elongate body between the proximal end and the distal end, wherein the proximal end of the second leg is connected to the second end of the bridge, wherein the second leg is solid in cross-section and has a second elongate groove on an exterior surface thereof, the second elongate groove extending an entire length of the elongate body from the distal end to the proximal end thereof, and wherein the second groove further extends into the second end of the bridge and is partially defined by perimetric surfaces of the bridge.

20. The staple of claim 19, wherein the one or more curves comprising a laterally curved shape, and wherein said bridge lies in a plane normal to axes of the staple legs.

21. The staple of claim 19, further comprising:
a third groove on the exterior surface of the first leg, wherein the third groove is oriented substantially perpendicular to and intersects with the first elongate groove; and
a fourth groove on the exterior surface of the second leg, wherein the fourth groove is oriented substantially perpendicular to and intersects with the second elongate groove.

* * * * *